US012557972B2

(12) United States Patent
Ji

(10) Patent No.: US 12,557,972 B2
(45) Date of Patent: Feb. 24, 2026

(54) INSERTION UNIT AND DETACHABLE ENDOSCOPE COMPRISING THE SAME

(71) Applicant: TAEWOONG MEDICAL CO., LTD., Gimpo-si (KR)

(72) Inventor: Hyun Soo Ji, Seoul (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 527 days.

(21) Appl. No.: 18/155,406

(22) Filed: Jan. 17, 2023

(65) Prior Publication Data

US 2023/0225591 A1     Jul. 20, 2023

(30) Foreign Application Priority Data

Jan. 14, 2022    (KR) ........................ 10-2022-0006189

(51) Int. Cl.
*A61B 1/005* (2006.01)
*A61B 1/00* (2006.01)

(52) U.S. Cl.
CPC ...... *A61B 1/00105* (2013.01); *A61B 1/00112* (2013.01); *A61B 1/00142* (2013.01); *A61B 1/00098* (2013.01)

(58) Field of Classification Search
CPC .............. A61B 1/00105; A61B 1/0057; A61B 1/00142; A61B 1/00112; A61B 1/00098; A61B 1/00128; A61B 1/00133; A61B 1/273
See application file for complete search history.

(56) References Cited

U.S. PATENT DOCUMENTS

| | | | | |
|---|---|---|---|---|
| 2012/0004503 A1* | 1/2012 | Kawaura | ............ | A61B 1/00128 |
| | | | | 600/104 |
| 2020/0367732 A1* | 11/2020 | Yamaya | ............. | A61B 1/00098 |
| 2022/0265967 A1* | 8/2022 | Alhadeff | ........... | A61M 25/0136 |
| 2022/0304549 A1* | 9/2022 | Iijima | ................ | A61B 1/00105 |

FOREIGN PATENT DOCUMENTS

| | | |
|---|---|---|
| JP | H07-184848 A | 7/1995 |
| JP | 2007-000427 A | 1/2007 |
| JP | 2021-041159 A | 3/2021 |

* cited by examiner

*Primary Examiner* — Michael J Carey
*Assistant Examiner* — Olivia Grace Starkey
(74) *Attorney, Agent, or Firm* — Bridgeway IP Law Group, PLLC; Jihun Kim

(57)     ABSTRACT
An insertion unit for a detachable endoscope, the insertion unit including a housing having a hollow formed penetrating both ends of the housing but being isolated from an outside of the housing; a first intermediate connection part inserted into an inside of the housing to penetrate the both ends of the housing; and a second intermediate connection part spaced apart from the first intermediate connection part and inserted penetrating the hollow.

7 Claims, 10 Drawing Sheets

INSERTION UNIT AND DETACHABLE ENDOSCOPE COMPRISING THE SAME

CROSS REFERENCE TO RELATED APPLICATION

The present application claims priority to Korean Patent Application No. 10-2022-0006189, filed Jan. 14, 2022, the entire contents of which is incorporated herein for all purposes by this reference.

BACKGROUND OF THE DISCLOSURE

Field of the Disclosure

The present disclosure relates to a device, and more particularly to an insertion unit and a detachable endoscope including the same.

Background Art

In general, a surgery using an endoscope is to insert an endoscope equipped with a camera and a surgery tool through a small hole without making a large incision in the body of a patient, and then proceed with the surgery while observing the affected part of the patient through the image taken by the endoscope in the body. In particular, the endoscopic surgery starting from laparoscopic surgery has advantages in that the incision region is smaller than that of laparotomy, so the scar region is also small, and there is little bleeding, which leads to the quick patient recovery after the surgery.

The conventional endoscopes are integrally constituted with an insertion part intended to be inserted into the human body and an operation part that operates the insertion part, and a plurality of channels and guides are embedded through the inside of each part. In particular, an image sensing device such as an expensive CCD is provided at the front end of the insertion part inserted into the body. Therefore, it is difficult to separate only the insertion part from the operation part and replace it with a new one. To overcome this problem, in line with the trend of strengthening the sanitary function of medical endoscopes, various types of detachable endoscopes are being used in which an insertion part intended to be inserted into the body and an operation part for operating the insertion part are connected to each other when being used, or separated from each other when being stored.

However, the conventional detachable endoscope has a problem in that contaminants introduced through the insertion part during the endoscopic procedure enter the inside of the coupled operation part by the medium of the intermediate connection part. In this case, due to the nature of the operation part having a complex internal structure, it is difficult to clean the inside thereof, and accordingly, since the inside of the operation part is contaminated, even though the insertion unit is replaced later, contaminants are re-introduced into the replaced insertion part during the procedure, resulting in the cause of infection in a patient undergoing the endoscopic procedure.

SUMMARY OF THE DISCLOSURE

A technical problem to be addressed by the present disclosure is to provide a detachable endoscope capable of preventing contamination of the inside of an operation part by structurally separating an insertion part and the operation part.

Technical drawbacks, which the present disclosure is to address, are limited to the aforementioned ones, and unmentioned or other technical drawbacks may be clearly appreciated from the following detailed description by a person having ordinary skill in the art to which the present disclosure belongs.

To accomplish the above-described technical objects, an insertion unit for a detachable endoscope according to an example of this disclosure may include a housing having a hollow formed penetrating both ends of the housing but being isolated from an outside of the housing; a first intermediate connection part inserted into an inside of the housing to penetrate the both ends of the housing; and a second intermediate connection part spaced apart from the first intermediate connection part and inserted penetrating the hollow.

According to an example of this disclosure, a plurality of the first intermediate connection parts may be provided, and the plurality of the first intermediate connection parts may be arranged to be spaced apart along an inner circumference direction of the housing and to surround the hollow.

According to an example of this disclosure, the insertion unit for a detachable endoscope may further include an elastic member disposed inside the hollow and between a stepped part included in the hollow and one end of the second intermediate connection part to provide elastic force to the second intermediate connection part.

According to an example of this disclosure, the insertion unit for a detachable endoscope may further include a curved connection part connected to one end of the second intermediate connection part and at least partially curved with respect to a longitudinal direction of the second intermediate connection part.

According to an example of this disclosure, at each of both ends of the second intermediate connection part, a sealing member for sealing a space between the second intermediate connection part and the hollow may be provided.

To accomplish the above-described technical objects, a detachable endoscope according to an example of this disclosure may include an insertion unit according to any one of claims 1 to 5, whose one end is intended to be inserted into a body; an operation unit coupled to another end of the insertion unit, and operating the one end of the insertion unit to perform a bending motion; and a detachment unit for detachably coupling the operation unit and the insertion unit.

According to an example of this disclosure, when the insertion unit and the operation unit are coupled, a discharge passage part may be formed between a first coupling end of the operation unit and a second coupling end of the insertion unit, which are disposed to face each other.

According to the examples of the present disclosure, the insertion unit and the detachable endoscope including the insertion unit have a sealed hollow formed inside the insertion unit, so that they can induce contaminants such as blood flowing thereinto during an endoscopic procedure to flow only into the aforementioned hollow. Additionally, the contaminants passing through the hollow of the insertion unit are discharged through the discharge passage part formed between the insertion unit and the operation unit when the two units are coupled, so that the inside of the operation unit can be prevented from being contaminated, thereby addressing the cleaning problem of the operation unit, and enabling its reuse.

The effects of the present disclosure are not limited to the aforementioned effects, but should be understood as including all effects that can be inferred from the configuration provided by the description or claims of the present application.

DETAILED DESCRIPTION OF THE DISCLOSURE

Figure 1:
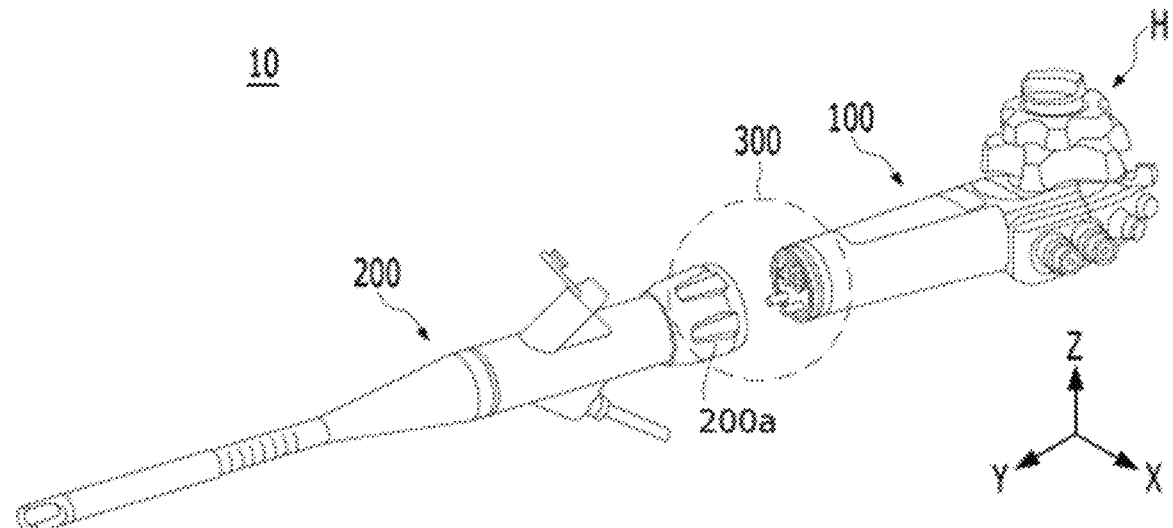
FIG. 1 is a perspective view showing a detachable endoscope according to an embodiment of the present disclosure.

Hereinafter, embodiments of the present disclosure will be described with reference to the accompanying drawings. However, the disclosure can be embodied in various different forms, and the scope of the disclosure should not be construed as being limited to the embodiments described herein. In the drawings, in order to describe clearly the disclosure, parts not related to the description are omitted, and like reference signs will be given to like constitutional elements throughout the specification.

As used herein, "connecting(or combining)" a part with another part (or "bring" a part into contact or touch with another part) may refer to a case where they are "indirectly connected" to each other with other element intervening therebetween, as well as a case where they are directly connected. Further, when a part "includes(or comprises)" a component, it means not that the part excludes other component, but instead that the part may further include other component unless expressly stated to the contrary.

The terms used herein are used to merely describe specific embodiments, but are not intended to limit the disclosure. Singular expressions may include the meaning of plural expressions unless the context clearly indicates otherwise. The terms such as "include (or comprise)", "have (or be provided with)", and the like are intended to indicate that features, numbers, steps, operations, components, parts, or combinations thereof written in the following description exist, and thus should not be understood as that the possibility of existence or addition of one or more different features, numbers, steps, operations, components, parts, or combinations thereof is excluded in advance.

Hereinafter, embodiments of this disclosure will be described in detail with reference to the accompanying drawings.

Figure 2:
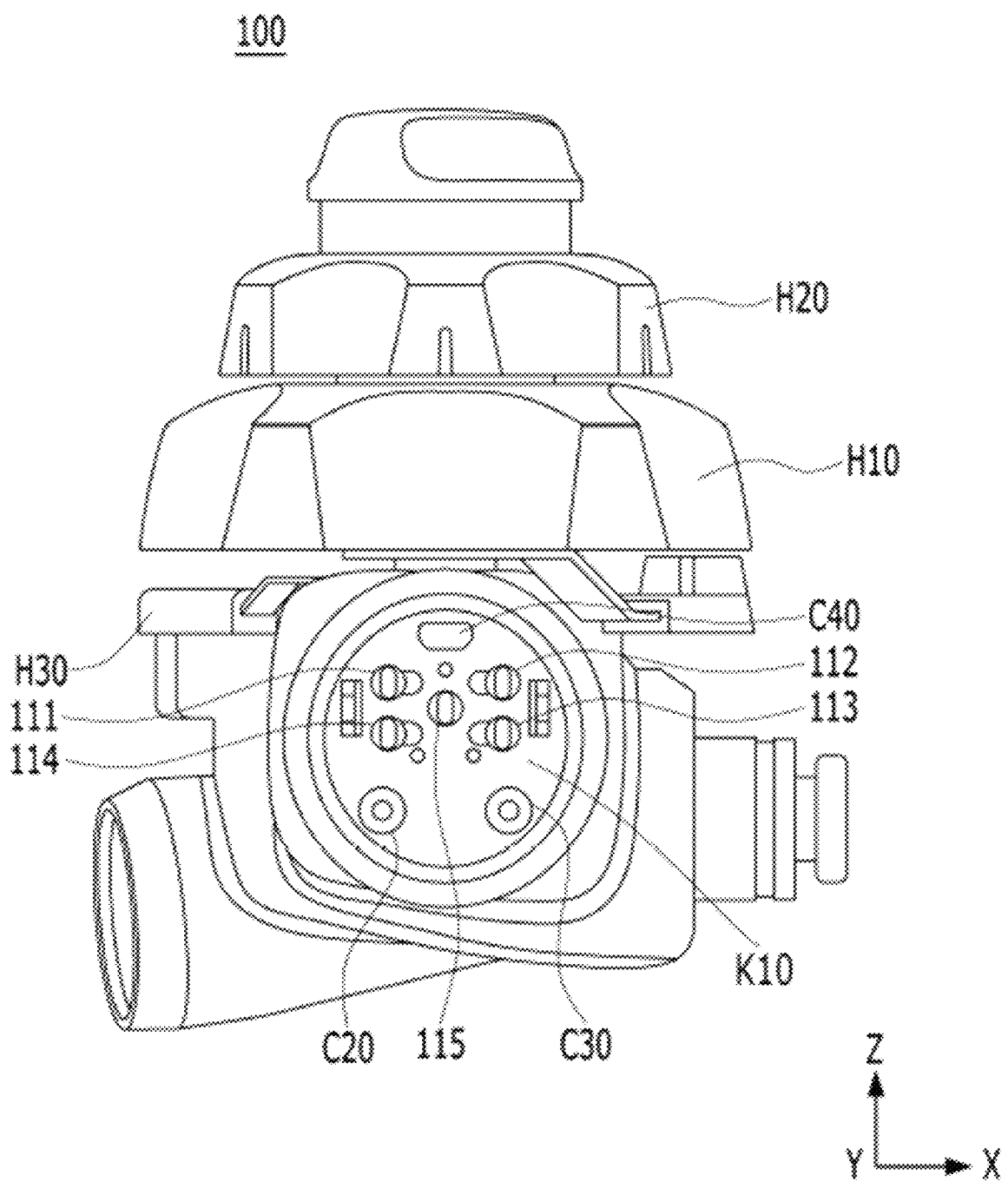
FIG. 2 is a front view showing one end of an operation unit provided in a detachable endoscope according to an embodiment of the present disclosure.
Figure 3:
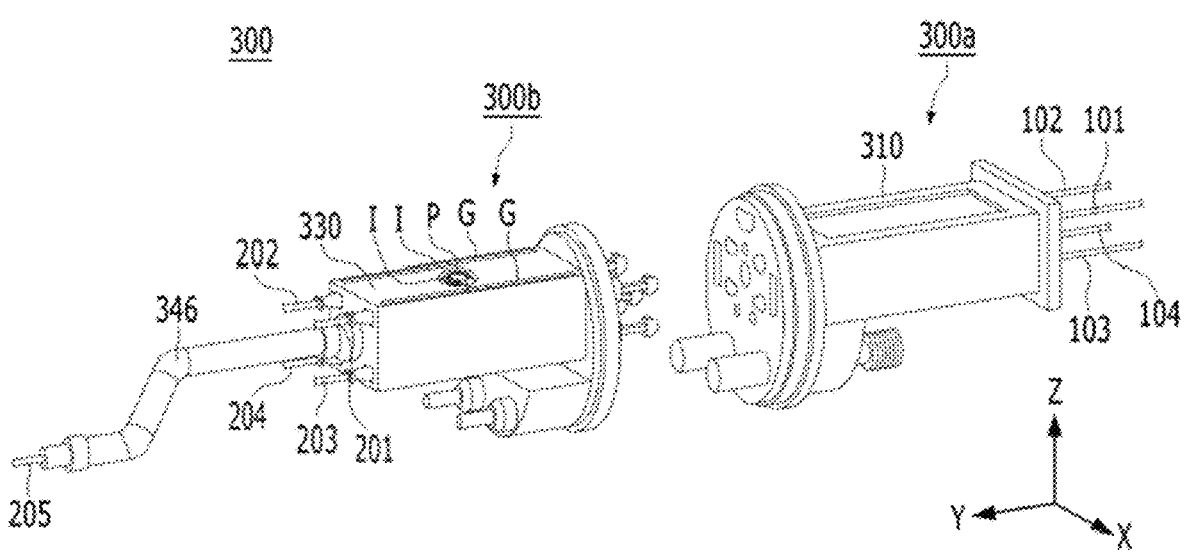
FIG. 3 is a perspective view showing a state before the coupling of a first detachment module and a second detachment module provided in a detachment unit according to an embodiment of the present disclosure.
Figure 4:
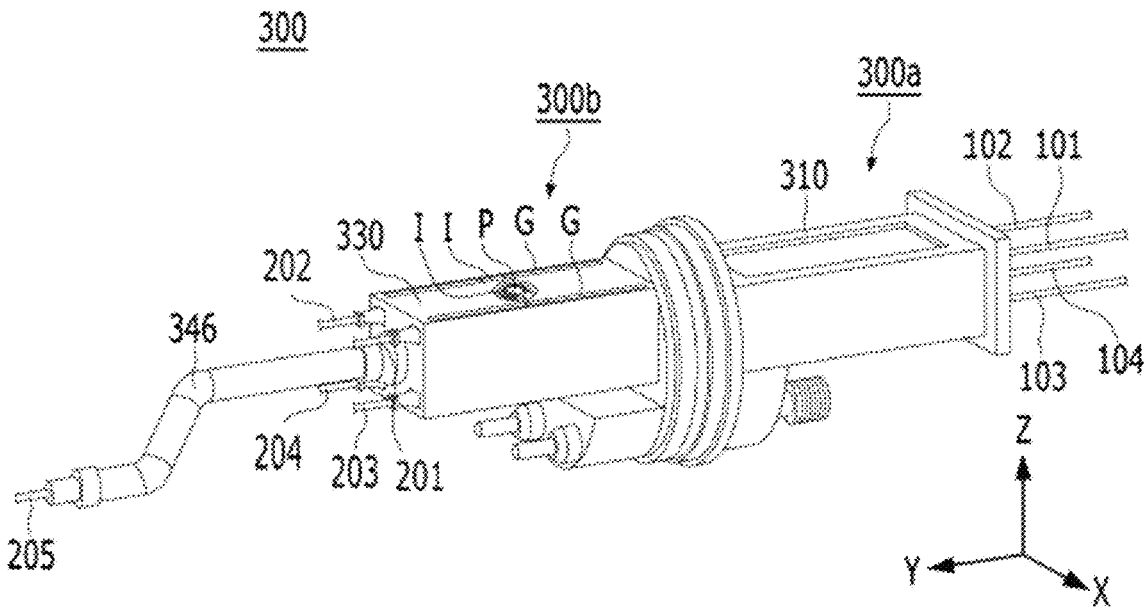
FIG. 4 is a perspective view showing a state in which a first detachment module and a second detachment module provided in a detachment unit according to an embodiment of the present disclosure are coupled to each other.
Figure 5:
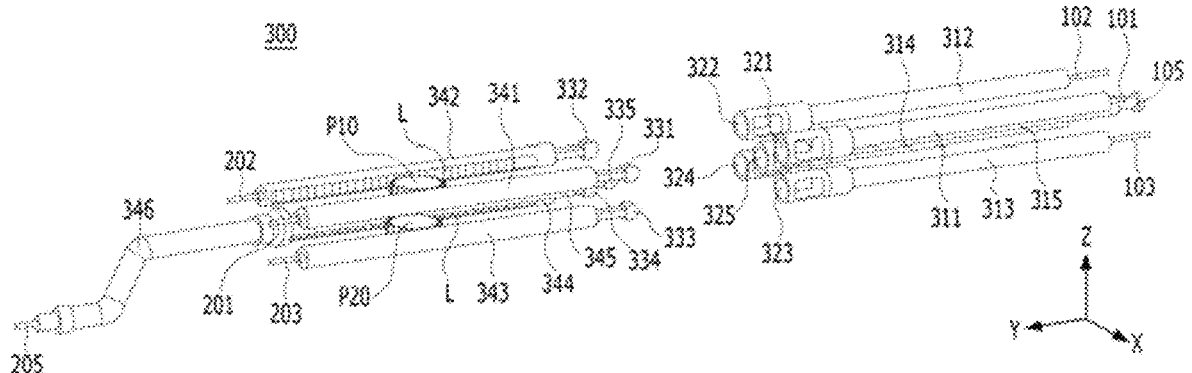
FIG. 5 is a perspective view showing the inside of the first detachment module and the second detachment module in a state before they are coupled in FIG. 3.
Figure 6:
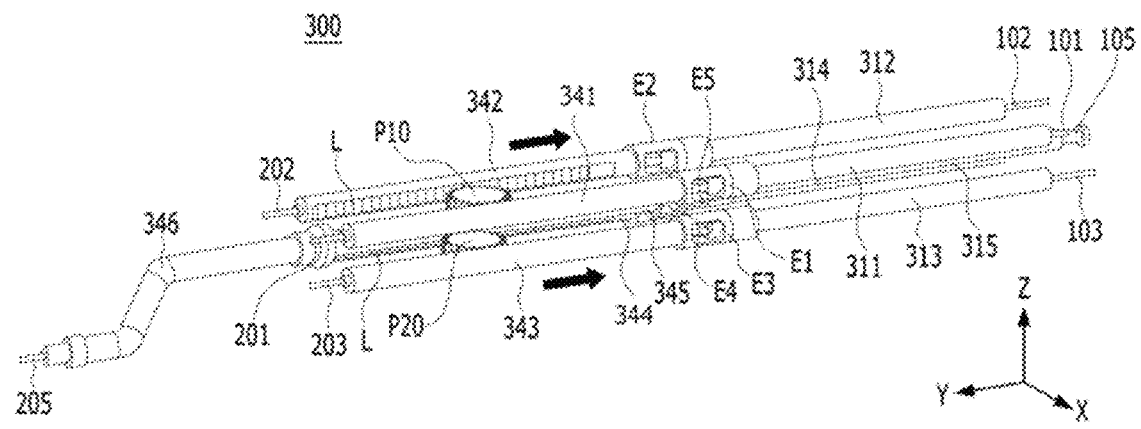
FIG. 6 is a perspective view showing the inside of the first detachment module and the second detachment module in a coupled state of FIG. 4.
Figure 7A:
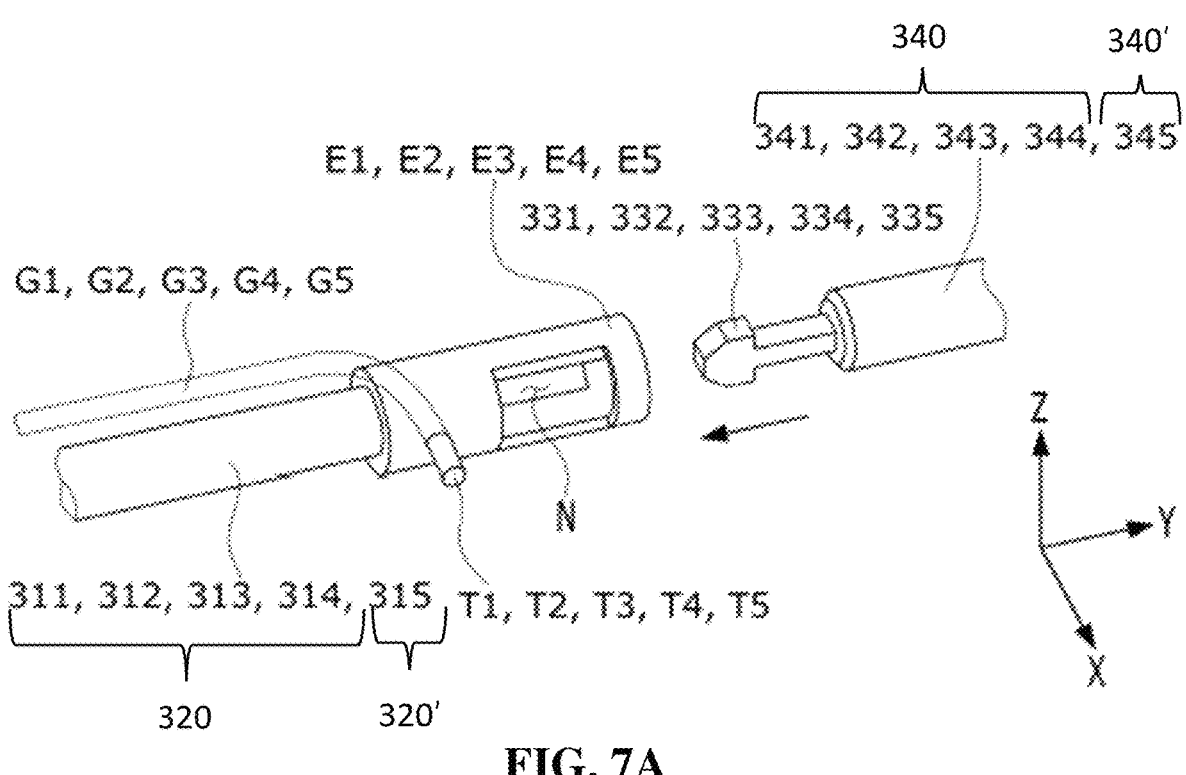
FIG. 7A is a perspective view showing a state before an intermediate connection part and an insertion end connection part provided in the detachable endoscope according to an embodiment of the present disclosure are coupled to each other.
Figure 7B:
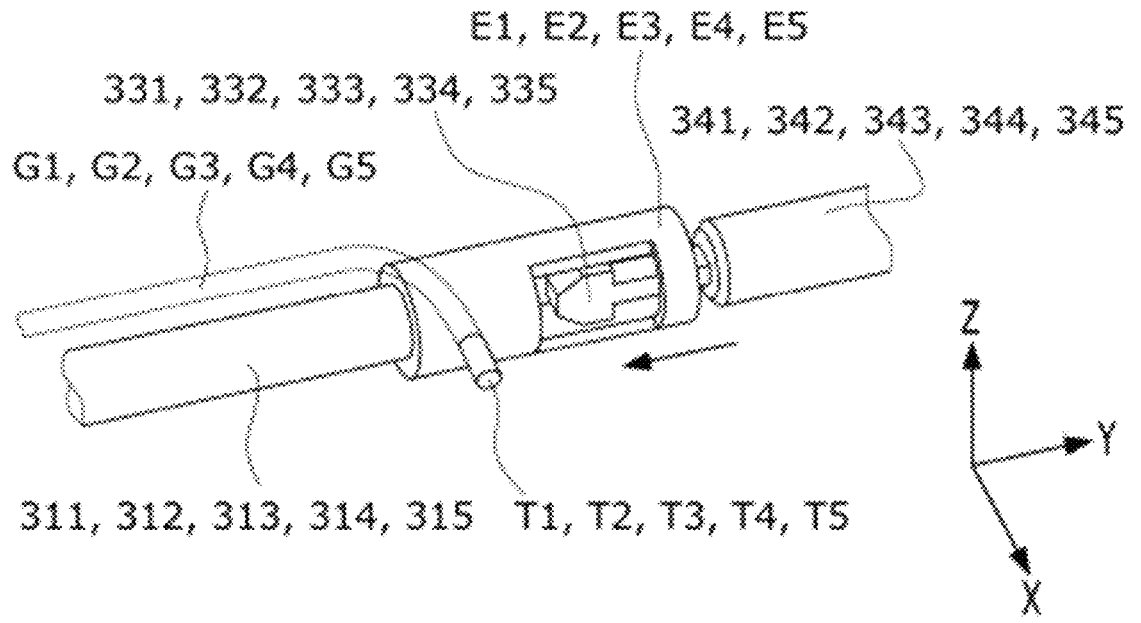
FIGS. 7B and 7C are perspective views showing states before the coupling of the intermediate connection part and the insertion end connection part is completed.
Figure 7C:
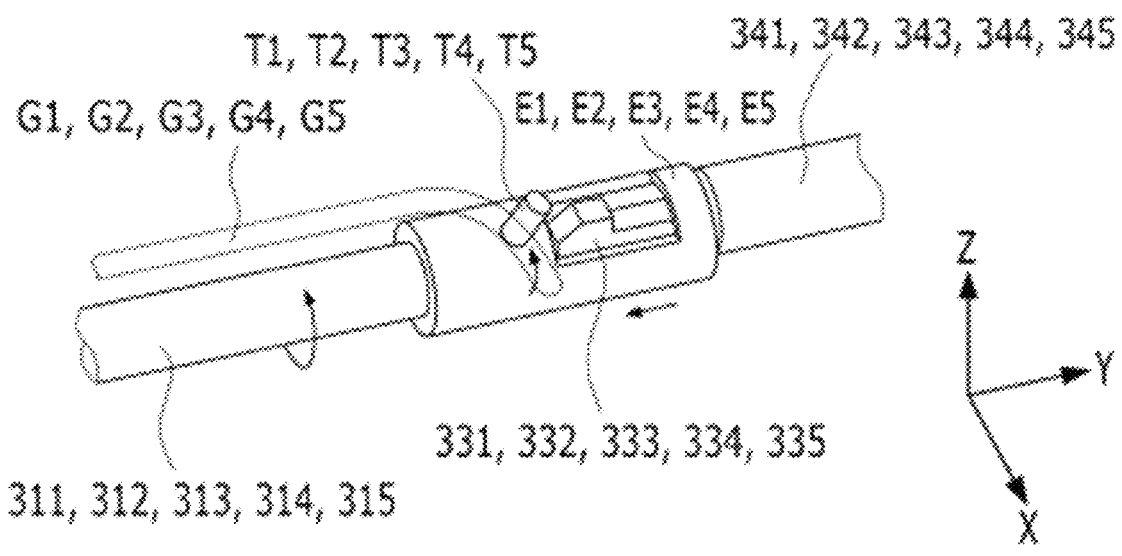
Figure 7D:
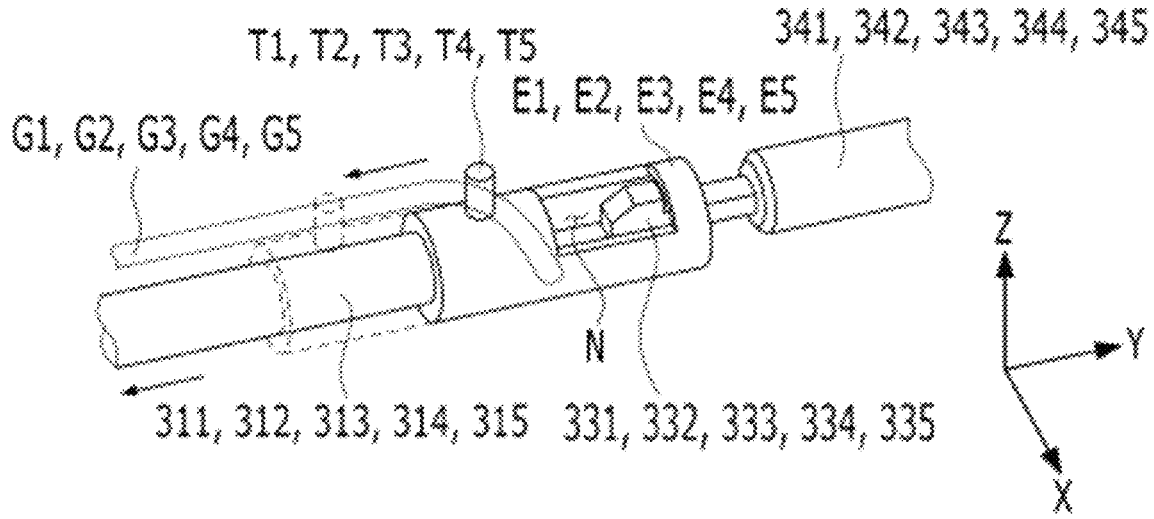
FIG. 7D is a perspective view showing a state in which the intermediate connection part and the insertion end connection part are coupled.

FIG. 1 is a perspective view showing a detachable endoscope according to an embodiment of the present disclosure. FIG. 2 is a front view showing one end of an operation unit provided in a detachable endoscope according to an embodiment of the present disclosure. FIG. 3 is a perspective view showing a state before the coupling of a first detachment module and a second detachment module provided in a detachment unit according to an embodiment of the present disclosure. FIG. 4 is a perspective view showing a state in which a first detachment module and a second detachment module provided in a detachment unit according to an embodiment of the present disclosure are coupled to each other. FIG. 5 is a perspective view showing the inside of the first detachment module and the second detachment module in a state before they are coupled in FIG. 3. FIG. 6 is a perspective view showing the inside of the first detachment module and the second detachment module in a coupled state of FIG. 4. And FIG. 7A is a perspective view showing a state before an intermediate connection part and an insertion end connection part provided in the detachable endoscope according to an embodiment of the present disclosure are coupled to each other. FIGS. 7B and 7C are perspective views showing states before the coupling of the intermediate connection part and the insertion end connection part is completed. FIG. 7D is a perspective view showing a state in which the intermediate connection part and the insertion end connection part are coupled.

Referring to FIGS. 1 to 6 and FIGS. 7A to 7D, a detachable endoscope 10 may be a device for inspecting and performing medical procedures on organs inside a body. Here, the target part for the inspection and medical procedure may be, for example, the duodenum.

The detachable endoscope 10 may include an operation unit 100, an insertion unit 200, and a detachment unit 300. In addition, the detachable endoscope 10 may further include a joint unit (not shown) electrically connected to an endoscope control and management system (not shown).

The operation unit 100 is a part that the user manipulates to control the operation of the insertion unit 200, and may include an operation module H. In this case, the operation module H may include a first operation part H10, a second operation part H20, and a third operation part H30.

To one end (hereinafter, a first coupling end) of the operation unit 100, the detachable insertion unit 200 can be selectively connected. In the state in which the insertion unit 200 is coupled to the operation unit 100, the user can rotate the first operation part H10 in left and right directions, so that the front end (hereinafter, referred to as an insertion end)

of the insertion unit 200 can be caused to perform a bending motion in up and down directions, or can rotate the second operation part H20 in left and right directions, so that the aforementioned insertion end can be caused to perform a bending motion in left and right directions. Additionally, the user can control the pivoting of a force applying module 400 to be described later by rotating the third operation part H30 in one direction.

The first operation part H10 may be provided with a lower sprocket (not shown) and a lower chain (not shown) meshed therewith, and the second operation part H20 may be provided with an upper sprocket (not shown) and an upper chain (not shown) meshed therewith. In this case, when the first operation part H10 and/or the second operation part H20 are/is rotated by the user's manipulation, the lower sprocket and/or the upper sprocket rotate(s), and this rotational motion can be converted into reciprocating rectilinear motion by the lower chain and/or the upper chain.

The lower chain and the upper chain may be connected to the inside of the insertion unit 200 by the medium of a first, second, third and fourth connection wires 101, 102, 103 and 104 and a first, second, third and fourth operation wires 201, 202, 203 and 204, which will be described later. In this case, by the reciprocating rectilinear motion of the upper chain and/or the lower chain, the first, second, third, and fourth connection wires 101, 102, 103, 104 and the first, second, third, and fourth operation wires 201, 202, 203, and 204 are selectively linearly moved, so that the insertion end of the insertion unit 200 connected to the first, second, third, and fourth operation wires 201, 202, 203, and 204 can be bent in the up and down directions or in the left and right directions. At this time, the user can adjust the bending amount of the insertion end by appropriately changing the rotation angle of the first operation part H10 and/or the second operation part H20.

In this case, the rotation of the lower sprocket and the upper sprocket may be made by the manual rotational manipulation of the user who holds the first operation parts H10 and the second operation part H20 provided in the operation module H. However, the present disclosure is not limited to this, but it may also be constituted by connecting a rotational axle connected to each of the lower sprocket and the upper sprocket with a driving means such as an electric motor, and using a separate remote control means for controlling the driving means.

The third operation part H30 may be connected to a lifting unit (not shown) disposed inside the operation unit 100. In this case, the lifting unit may be operated, as an embodiment, in a hydraulic manner. In this case, the lifting unit may include a hydraulic pressure supply part (not shown) and a linear movement shaft (not shown). In this case, the hydraulic pressure supply part may supply hydraulic pressure to the linear movement shaft connected to an intermediate connection member 105 based on the manipulation of the third operation part H30.

At this time, when the third operation part H30 is rotated in one of the left and right directions (hereinafter, referred to as the operation direction) by the user in a state in which the insertion unit 200 is coupled to the operation unit 100, the linear movement shaft can move backward (−Y axis direction) due to the hydraulic pressure supplied by the hydraulic pressure supply part.

Accordingly, the intermediate connection member 105 and a second intermediate connection body 315, and a second insertion end connection body 345 coupled thereto and the fifth operation wire 205 move in the direction of being pulled toward the operation unit 100 (hereinafter, referred to as the force applying direction) (e.g., −Y axis direction), so that force can be applied to the force applying module 400 connected to the fifth operation wire 205 in the force applying direction (−Y axis direction). Accordingly, the force applying module 400 can pivot in the first rotation direction R1 toward the operation unit 100 around the pivot axis C (see FIG. 8).

Meanwhile, the present disclosure is not limited to the above-described embodiment, but the lifting unit may also rotate the force applying module 400 by being operated in a manner other than the hydraulic operation manner. However, for the convenience of description, hereinafter, an embodiment in which the lifting unit operates in a hydraulic manner will be mainly described.

The third operation part H30 may be provided with an elastic part (not shown). This elastic part may be compressed and deformed as the third operation part H30 is rotated in the operation direction by the user. Thereafter, by generating an elastic restoring force in the opposite direction to the operation direction and returning the third operation part H30 to its original position when the force applied to the third operation part H30 is removed, the hydraulic pressure applied to the linear movement shaft is removed, so that the intermediate connection member 105, the second insertion end connection part 340', and the fifth operation wire 205 can move back in an opposite direction (Y axis direction) to the force applying direction. Accordingly, the force applying module 400 can rotate in the second rotation direction R2 opposite to the first rotation direction R1, and can return to the original position.

A part (i.e., the insertion end) of the insertion unit 200 may be inserted into the body during an endoscopic procedure. In this case, the insertion end of the insertion unit 200 may be an end among both ends of the insertion unit 200, which is opposite to the end coupled to the operation unit 100 (hereinafter, referred to as a second coupling end). At the insertion end, an illuminating and photographing unit may be provided which has a light source for illuminating the inside of the body, and an image sensor for photographing the inside of the body.

The aforementioned force applying module 400 may be disposed at the insertion end of the insertion unit 200. Specifically, the force applying module 400 may be disposed in the opening provided at the aforementioned insertion end. In this case, the force applying module 400 may be installed to be pivotable around a connection axis C perpendicular to the longitudinal direction (Y axis direction) of the insertion unit 200.

During an endoscopic procedure, a separate procedure equipment may be inserted into the insertion unit 200 through an insertion structure for connection provided in the detachable endoscope 10. This procedure equipment may pass through the inner passage (not shown) of the insertion unit 200, and moves to the outside of the insertion end through the above-mentioned opening to perform a medical procedure on the duodenum or the like.

In this case, the force applying module 400 may apply force to the procedure equipment, which has been moved to the outside of the insertion end through the opening, to bend the procedure equipment toward a position where the medical procedure is required. For example, during an endoscopic procedure, by rotating the force applying module 400 in the first rotation direction R1 using the third operation part H30, the procedure equipment can be bent in a direction corresponding to the first rotation direction R1. In the case where the endoscopic procedure is completed or the procedure equipment needs to be replaced, by removing the force applied to the third operation part H30 and returning the force applying module 400 to its original position, it is possible to remove the force applied to the procedure equipment and return it to the state before the bending.

In an example, the insertion unit 200 may have an elongate cylindrical shape with a hollow formed therein. At least a portion of the insertion unit 200 may be formed with a flexible material, so that the bending direction can be adjusted by the operation unit 100 as described above. For example, a cover forming the outer surface of the insertion unit 200 may be formed with a flexible tube material such as a resin composition.

Meanwhile, the operation unit 100 may include a manipulation switch and a manipulation button for injecting or discharging liquid and gas used during an endoscopic procedure. A part (e.g., the second coupling end or its periphery) of the insertion unit 200 detachably coupled with the first coupling end of the operation unit 100 via the detachment unit 300 may be provided with an entrance through which a medical procedure tool such as an endoscopic procedure tool having a clip is protruded from or retracted into the insertion unit 200, and with a cap for opening and closing the entrance.

As exemplarily shown in FIGS. 2 to 4, a support cover K10 may be provided at the first coupling end of the operation unit 100. In this case, an air supply channel C30 for supplying air, a water supply channel C20 for supplying water, and a terminal C40 electrically connected to an illuminating and photographing part provided at the above-described insertion end may be formed to pass through the support cover K10.

The detachment unit 300 may detachably connect the operation unit 100 and the insertion unit 200. In this case, the detachment unit 300 may include a first detachment module 300*a* and a second detachment module 300*b* that are detachably coupled to each other. The operation unit 100 and the insertion unit 200 may be connected or separated by the coupling or decoupling of the first detachment module 300*a* and the second detachment module 300*b*.

The first detachment module 300*a* may be arranged to be inserted into the housing of the operation unit 100, and may include a first module body 310, a first intermediate connection part, and a second intermediate connection part. And the second detachment module 300*b* may be arranged to be inserted into the housing of the insertion unit 200, and may be provided with a second module body 330, a first insertion end connection part, and a second insertion end connection part.

In this case, although reference numerals are not indicated in the drawings, for the convenience of description, hereinafter, the first intermediate connection part will be denoted by reference number 320, and the second intermediate connection part will be denoted by reference number 320'. Additionally, the first insertion end connection part will be denoted by reference number 340, and the second insertion end connection part will be denoted by reference number 340'.

The first module body 310 may be a housing in which a first middle hollow and a second middle hollow are formed penetrating both ends along the longitudinal direction (Y axis direction). These first and second middle hollows may be arranged on the same line to be communicated with each other, along the through holes for connection 111, 112, 113, 114, and 115 (in FIG. 2) provided in the support cover K10 and the longitudinal direction (Y axis direction).

The first intermediate connection part 320 may connect the operation module H and the first insertion end connection part 340 to be described later by the medium of the first, second, third, and fourth connection wires 101, 102, 103, and 104. At this time, the first intermediate connection part 320 may be provided with two pairs of first intermediate connection bodies 311, 312, 313, and 314, and first connection ends E1, E2, E3, and E4 respectively provided thereto.

In an example, the first intermediate connection bodies 311, 312, 313, and 314 may be bars having an elongate cylindrical shape. The first intermediate connection bodies 311, 312, 313, and 314 may be inserted penetrating the first middle hollow of the first module body 310. At this time, both ends of the first intermediate connection bodies 311, 312, 313, and 314 may be disposed at least partially outside the first module body 310.

The first connection ends E1, E2, E3, and E4 may be detachably connected to first engaging members 331, 332, 333, and 334 to be described later. The first connection ends E1, E2, E3, and E4 may be disposed at one ends of the first intermediate connection bodies 311, 312, 313, and 314, and these one ends of the first intermediate connection bodies 311, 312, 313, and 314 may be ends facing the insertion unit 200. The other ends of the first intermediate connection bodies 311, 312, 313, and 314 may be connected to one ends of the first, second, third, and fourth connection wires 101, 102, 103, and 104, and at this time, the other ends of the first, second, third, and fourth connection wires 101, 102, 103, and 104 may be connected to the lower chain or the upper chain provided in the first operation part H10 or the second operation part H20.

In this case, as the user manipulates the first operation part H10 or the second operation part H20, the rotational motion of the lower sprocket or the upper sprocket can be converted into reciprocating rectilinear motion by the lower chain or upper chain, and subsequently, the first, second, third, and fourth connection wires 101, 102, 103, and 104 connected to the lower chain or the upper chain can perform reciprocating rectilinear motion. Accordingly, the first intermediate connection bodies 311, 312, 313, and 314 connected to the first, second, third and fourth connection wires 101, 102, 103, and 104, and the first connection ends E1, E2, E3, and E4 can perform reciprocating rectilinear motion along a direction parallel to the longitudinal direction (Y axis direction).

The first connection ends E1, E2, E3, and E4 may be formed with a larger outer diameter than the outer diameter of the first intermediate connection bodies 311, 312, 313, and 314. At this time, elastic members S, which the intermediate connection bodies 311, 312, 313, and 314 are inserted penetrating, may be disposed between the first connection ends E1, E2, E3, and E4 and the first, second, third, and fourth connection wires 101, 102, 103, and 104. As the first intermediate connection bodies 311, 312, 313, and 314 are pressed by the insertion end connection part 340 during the coupling process, these elastic members are compressed and deformed, and can generate an elastic restoring force for returning the intermediate connection bodies 311, 312, 313, and 314 to their original positions. The elastic member S may be constituted with, for example, a coil spring.

The first connection ends E1, E2, E3, and E4 may be provided with first insertion grooves 321, 322, 323, and 324 into which the first engaging members 331, 332, 333, and 334 are inserted when the insertion unit 200 and the operation unit 100 are coupled to each other, and first guide projections T1, T2, T3, and T4 for guiding rotation of the first intermediate connection bodies 311, 312, 313, and 314.

The first insertion grooves 321, 322, 323, and 324 may be formed concavely in the longitudinal direction (e.g., −Y axis direction) inward from the first connection ends E1, E2, E3, and E4. The first insertion grooves 321, 322, 323, and 324 may be provided with penetration parts N formed to penetrate through the first connection ends E1, E2, E3, and E4 in a direction (X axis direction) perpendicular to the longitudinal direction (Y axis direction). The first insertion grooves 321, 322, 323, and 324 may be partially communicated with the outside through the penetration parts N. Additionally, the first engaging members 331, 332, 333, and 334 can be in an engaged state and secured in the first insertion grooves 321, 322, 323, and 324 by the penetration parts N.

The first guide projections T1, T2, T3, and T4 can guide the rotational motion of the first intermediate connection bodies 311, 312, 313, and 314. The first guide projections T1, T2, T3, and T4 may be formed to protrude toward the outside in the radial direction from the first connection ends E1, E2, E3, and E4 of the first intermediate connection bodies 311, 312, 313, and 314.

In the case where after the insertion of the first engaging members 331, 332, 333, and 334 into the first insertion grooves 321, 322, 323, and 324, the second insertion end connection part 340' is pulled and moved backward (−Y axis direction) by the manipulation of the operation module H, the first guide projections T1, to T2, T3, and T4 can move along the first guide slits G1, G2, G3, and G4 formed in the first module body 310.

The first guide slits G1, G2, G3, and G4 may include a curved line part that is curved and extended from one side of the first module body 310 to the other side thereof, and a straight line part connected to this curved line part and extending backward (−Y axis direction) parallel to the longitudinal direction of the first intermediate connection bodies 311, 312, 313, and 314.

In the case where the first insertion end connection part 340 is pulled to move backward (−Y axis direction), the first guide projections T1, T2, T3, and T4 first rotate along the curved line part, and thereby the first intermediate connection bodies 311, 312, 313, and 314 can be rotated and simultaneously guided to move backward (−Y axis direction) by the first guide projections T1, T2, T3, and T4. Thereafter, as the first insertion end connection part 340 moves further backward (−Y axis direction), the guide projections T1, T2, T3, and T4 passing through the curved part move linearly along the straight line part, and accordingly, the first engaging members 331, 332, 333, and 334 are engaged inside the first insertion grooves 321, 322, 323, and 324, and thereby the first intermediate connection part 320 and the second insertion end connection part 340 are coupled so that they are not separated during the endoscopic procedure, and can operate integrally by manipulating the operation module H.

The second intermediate connection part 320' may connect the operation module H and the force applying module 400 disposed at the insertion end by the medium of the intermediate connection member 105. In this case, the second intermediate connection part 320' may be provided with one second intermediate connection body 315 and a second connection end E5.

The second intermediate connection body 315 may be inserted penetrating the second middle hollow spaced apart from the first middle hollow. At this time, both ends of the second intermediate connection body 315 may be disposed at least partially outside the first module body 310.

The second connection end E5 may be detachably connected to the second engaging member 335 to be described later. The second connection end E5 may be disposed at one end of the second intermediate connection body 315, and the intermediate connection member 105 may be provided at the other end of the second intermediate connection body 315. In this case, the intermediate connection member 105 may be connected to the third operation part H30 by the medium of the lifting unit.

As exemplarily shown in the drawings, the intermediate connection member 105 may be formed to protrude from the second intermediate connection body 315 toward the rear (−Y axis direction) in parallel with the longitudinal direction (Y axis direction). In this case, the rear end of the intermediate connection member 105 may be provided with a projection for engagement to engage with the linear movement shaft of the lifting unit. In this case, after the intermediate connection member 105 is inserted into an engagement groove (not shown) provided at the front end of the linear movement shaft, the engagement projection can be engaged and secured in the engagement groove. By this, the intermediate connection member 105 and the second intermediate connection body 315 can be coupled to the lifting unit. Meanwhile, the present disclosure is not limited to this, but as another embodiment, the intermediate connection member 105 may be connected to the linear movement shaft by the medium of a connection wire (not shown).

In this case, as the user manipulates the third operation part H30 in the operation direction, the linear movement shaft and the intermediate connection member 105 connected thereto can perform a rectilinear motion in the force applying direction (−Y axis direction) by the hydraulic pressure supplied from the hydraulic pressure supply part. At the same time, the second intermediate connection body 315 and the second connection end E5 may perform a rectilinear motion in the force applying direction (−Y axis direction).

A second insertion groove 325 and a second guide projection T5 may be formed at the second connection end E5, and the second guide projection T5 may move along the second guide slit G5 provided in the first module body 310 and may guide the movement of the second intermediate connection body 315. Other specific features of the second intermediate connection part 320' and the coupling method with the second insertion end connection part 340' are the same as or similar to those of the above-described first intermediate connection part 320, so redundant descriptions thereof will be omitted.

As described above, the first intermediate connection part 320 may include two pairs of first intermediate connection bodies 311, 312, 313, and 314. In this case, for the convenience of description, the two pairs of first intermediate connection bodies 311, 312, 313, and 314 will be referred to as a first-first intermediate connection body 311, a first-second intermediate connection body 312, a first-third intermediate connection body 313, and a first-fourth intermediate connection body 314.

In this case, two pairs of first middle hollows may be formed in the first module body 310, and the first-first, first-second, first-third, and first-fourth intermediate connection bodies 311, 312, 313, and 314 may be inserted penetrating them, respectively.

The first-first, first-second, first-third, and first-fourth intermediate connection bodies 311, 312, 313, and 314 may be arranged symmetrically with each other, within the first module body 310, in the width direction (X axis direction) and/or in the height direction (Z axis direction). Specifically, the first-first intermediate connection body 311 may be arranged symmetrically with the first-second intermediate connection body 312 in the width direction (X axis direction). At this time, the first-first intermediate connection body 311 may be arranged symmetrically with the first-third intermediate connection body 313 in the height direction (Z axis direction), and the first-third intermediate connection body 313 may be arranged symmetrically with the first-fourth intermediate connection body 314 in the width direction (X axis direction). Accordingly, the first-first intermediate connection body 311 and the first-second intermediate connection body 312 can be arranged side by side in a pair on the upper side inside the first module body 310, and the first-third intermediate connection body 313 and the first-fourth intermediate connection body 314 can be arranged side by side in a pair on the lower side inside the first module body 310.

In this case, the second middle hollow may extend beyond the inner region of the first module body 310, defined by the first-first, first-second, first-third, and first-fourth intermediate connection bodies 311, 312, 313, and 314, and as a result, the second intermediate connection part 320' may be surrounded by the first-first, first-second, first-third, and first-four intermediate connection bodies 311, 312, 313, and 314 to be located in the center.

The connection ends of the first and second intermediate connection bodies 311, 312, 313, 314, and 315, that is, the first-first connection end E1, the first-second connection end E2, and the first-third connection end E3, the first-fourth connection end E4, and the second connection end E5 may be arranged to protrude outward from the first module body 310 toward the insertion unit 200.

Additionally, the first connection wire 101, the second connection wire 102, the third connection wire 103, and the fourth connection wire 104 may be connected to the other ends of the first intermediate connection bodies 311, 312, 313, and 314, respectively, which are opposite to the first connection ends E1, E2, E3, and E4. And the above-described intermediate connection member 105 may be provided at the other end of the second intermediate connection body 315 opposite to the second connection end E5, so that the other ends can be connected to the lifting unit. In this case, each of the first intermediate connection bodies 311, 312, 313, and 314 may be disposed in the first module body 310 in a state of being inserted penetrating the elastic member S in the form of a coil spring.

As described above, the second detachment module 300b may be provided with the second module body 330, the first insertion end connection part 340, and the second insertion end connection part 340'.

The second module body 330 may be a housing in which a first insertion end hollow, and a second insertion end hollow HL penetrating both ends along a longitudinal direction (Y axis direction) are formed.

The first insertion end connection part 340 can transfer the force applied by the user's manipulation of the operation module H to the insertion end by the medium of the first, second, third, and fourth operation wires 201, 202, 203, and 204, so that the insertion end of the insertion unit 200 can perform a bending motion. In this case, the first insertion end connection part 340 may include two pairs of first insertion end connection bodies 341, 342, 343, and 344, which are provided with the first engaging members 331, 332, 333, and 334, respectively.

The first insertion end connection bodies 341, 342, 343, and 344 may be bars having an elongate cylindrical shape in an example. The first insertion end connection bodies 341, 342, 343, and 344 may be inserted penetrating the first insertion end hollow of the second module body 330. In this case, both ends of the first insertion end connection bodies 341, 342, 343, and 344 may be arranged protruding at least partially to the outside of the second module body 330.

Each of the first insertion end connection bodies 341, 342, 343, and 344 may have a rack gear part L on its one surface. Each of the rack gear parts L may be disposed on a surface among surfaces of the first insertion end connection body 341, 342, 343, or 344, which faces the center of the second module body 330. And, the rack gear parts L may extend along the longitudinal direction (Y axis direction) of the first insertion end connection bodies 341, 342, 343, and 344.

The first engaging members 331, 332, 333, and 334 can be inserted into the aforementioned first insertion grooves 321, 322, 323, and 324 of the first connection ends E1, E2, E3, and E4, and can be detachably coupled thereto.

The first engaging members 331, 332, 333, and 334 may be disposed at one ends of the first insertion end connection bodies 341, 342, 343, and 344, and the one ends of the first insertion end connection bodies 341, 342, 343, and 344 may be ends facing the operation unit 100. In this case, one ends of the first, second, third, and fourth operation wires 201, 202, 203, and 204 can be connected to the other ends of the first insertion end connection bodies 341, 342, 343, and 344, and the other ends of the first, second, third, and fourth operation wires 201, 202, 203, and 204 can be connected to the inside of the insertion ends.

At this time, the first engaging members 331, 332, 333, and 334 may be formed in a protruding length similar to the depth of the concaves inward in the longitudinal direction of the first insertion grooves 321, 322, 323, and 324, preferably in a shorter protruding length. Accordingly, when the first engaging members 331, 332, 333, and 334 are inserted into the first insertion grooves 321, 322, 323, and 324, a predetermined clearance may exist between the first engaging members 331, 332, 333, and 334 and the first insertion grooves 321, 322, 323, and 324.

The second insertion end connection part 340' can transfer the force applied by the user manipulating the third operation part H30 by the medium of the fifth operation wire 205 to the force applying module 400, so that the force applying module 400 can rotate. In this case, the second insertion end connection part 340' may include one second insertion end connection body 345, a curved connection part 346, and a second engaging member 335.

The second insertion end connection body 345 may be inserted penetrating the second insertion end hollow HL spaced apart from the first insertion end hollow. In this case, both ends of the second insertion end connection body 345 may be disposed at least partially outside the second module body 330.

The curved connection part 346 may be disposed between the second insertion end connection body 345 and the force applying module 400, and may have a hollow formed therein for accommodating the operation wire 205. The operation wire 205 may be disposed in the inner hollow of the curved connection part 346, and extend toward the force applying module 400 from the second insertion end connection body 345. In this case, one end of the operation wire 205 can be connected to the second insertion end connection body 345, and the other end of the operation wire 205 can be connected to the force applying module 400.

The curved connection part 346 may have a curved part curved with respect to the longitudinal direction (Y axis direction) of the second insertion end connection part 340'. Through this curved part, disposal state such as the bending direction, bending degree or the like of the operation wire 205 disposed inside the inner hollow of the curved connection part 346 can be adjusted.

Specifically, the second operation wire 205 may have one end connected to the second insertion end connection body 345 and the other end extending toward the insertion end. In this case, a part between the aforementioned one end and the other end of the second operation wire 205 can be bent and extended along the curved connection part 346. Accordingly, among the entire length of the second operation wire 205, the length extending past the curved connection part 346 may be disposed extending toward the insertion end inside the insertion unit 200 in the longitudinal direction (Y axis direction) to pass through the center of the insertion unit 200.

Additionally, the second insertion end connection part 340' can be placed without affecting the second insertion end connection part 340 disposed in a straight line within the limited space inside the second module body 330 through the curved connection part 346, so that the space utilization can be improved.

The second engaging member 335 may be inserted into the second insertion groove 325 of the second connection end E5 and detachably coupled thereto. The second engaging member 335 may be formed protruding outward in the longitudinal direction (–Y axis direction) at the opposite end of the curved connection part 346 among both ends of the second insertion end connection body 345. In this case, one end of the operation wire 205 can be connected to the other end of the second insertion end connection body 345, and the other end of the fifth operation wire 205 can be connected to the force applying module 400.

In this case, as the user manipulates the third operation part H30 in the operation direction, the linear movement shaft and the intermediate connection member 105 connected thereto and the second intermediate connection body 315 can perform a rectilinear motion in the force applying direction (–Y axis direction) by the hydraulic pressure supplied from the hydraulic pressure supply part.

In this case, a second insertion groove 325 and a second guide projection T5 can be formed at the second connection end E5, and the second guide projection T5 can move along the second guide slit G5 provided in the second module body 330, and can guide the movement of the second intermediate connection body 315. Other specific features of the second intermediate connection part 320' and the coupling method with the second insertion end connection part 340' and the operation manner after the coupling are the same as or similar to those of the above-described first intermediate connection part 320, so redundant descriptions thereof will be omitted.

As described above, the first insertion end connection part 340 may include two pairs of first insertion end connection bodies 341, 342, 343, and 344. In this case, for the convenience of description, the two pairs of first insertion end connection bodies will be referred to as the first-first insertion end connection body 341, the first-second insertion end connection body 342, the first-third insertion end connection body 343, and the first-fourth insertion end connection body 344.

In this case, two pairs of first insertion end hollows may be formed in the second module body 330, and the first-first, first-second, first-third, and first-fourth insertion end connection bodies 341, 342, 343, and 344 may be inserted penetrating these two pairs of first insertion end hollows, respectively.

The first-first, first-second, first-third, and first-fourth insertion end connection bodies 341, 342, 343, and 344 may be arranged symmetrically with each other in the width direction (X axis direction) and/or the height direction (Z axis direction) in the second module body 330.

Specifically, the first-first insertion end connection body 341 may be arranged symmetrically with the first-second insertion end connection body 342 in the width direction (X axis direction). Accordingly, the rack gear part L of the first-first insertion end connection body 341 and the rack gear part L of the first-second insertion end connection body 342 can be arranged to face each other.

Additionally, the first-first insertion end connection body 341 may be arranged symmetrically with the first-third insertion end connection body 343 in the height direction (Z axis direction), and the first-third insertion end connection body 343 may be arranged symmetrically with the first-fourth insertion end connection body 344 in the width direction (X axis direction). Accordingly, the third rack gear part L of the first-third insertion end connection body 343 and the fourth rack gear part L of the first-fourth insertion end connection body 344 may be arranged to face each other.

Accordingly, the first-first insertion end connection body 341 and the first-second insertion end connection body 342 can be arranged side by side in a pair on the upper side inside the second module body 330, and the first-third insertion end connection body 343 and the first-fourth insertion end connection body 344 can be arranged side by side in a pair on the lower side inside the second module body 330.

In this case, as described above, the second insertion end connection part 340' may be disposed in a region defined by being surrounded by the first-first, first-second, first-third, and first-fourth insertion end connection bodies 341, 342, 343, and 344 in the second module body 330. In this case, the second insertion end connection body 345, in one embodiment, can extend through the middle of the first-first, first-second, first-third, and first-fourth insertion end connection bodies 341, 342, 343, and 344.

In the above case, the second module body 330 may be provided with a pinion gear unit P. In this case, the pinion gear unit P may include a first pinion gear P10 and a second pinion gear P20 (see FIGS. 5 and 6).

The first pinion gear P10 may be disposed between the first-first insertion end connection body 341 and the first-second insertion end connection body 342, so that it can be meshed with the first rack gear part L of the first-first insertion end connection body 341 and the second rack gear part L of the first-second insertion end connection body 342 at the same time. In this meshed state, the first pinion gear P10 may rotate around the first central axle part perpendicular to the longitudinal direction (Y axis direction) according to the user's manipulation of the operation module H.

The second pinion gear P20 may be disposed between the first-third insertion end connection body 343 and the first-fourth insertion end connection body 344, so that it can be meshed with the third rack gear part L of the first-third insertion end connection body 343 and the fourth rack gear part L of the first-fourth insertion end connection body 344 at the same time. In this meshed state, the second pinion gear P20 may rotate around the second central axle part perpendicular to the longitudinal direction (Y axis direction) according to the user's manipulation of the operation module H.

The second central axle part may be disposed on the same line as the first central axle part, but may be configured to be separated from each other and independently rotatable. Accordingly, while the first pinion gear P10 and the second pinion gear P20 rotate around the first central axle part or the second central axle part, they can avoid interfering with (or hindering) each other's rotational movements. The second module body 330 may be provided with a guide hole (not shown) which is formed penetrating in the longitudinal direction (Y axis direction) while passing past the center of a region surrounded by the first-first, first-second, first-third, and first-fourth insertion end connection bodies 341, 342, 343, and 344. In this regard, the guide hole may be disposed between the first pinion gear and the second pinion gear so as not to interfere with rotation of the pinion gears. In this case, the second insertion end connection body 345 can be disposed inside the above-described guide hole, and can perform reciprocating rectilinear motion in parallel with the longitudinal direction (Y axis) inside the guide hole.

The second module body 330 may be provided with straight line guide slits G extending along the longitudinal direction (Y axis direction) on its upper and lower surfaces. The straight line guide slits G may include a pair of 'upper surface straight line guide slits' provided on the upper surface of the second module body 330 to face the first-first insertion end connection body 341 and the first-second insertion end connection body 342, respectively, and a pair of 'lower surface straight line guide slits' provided on the lower surface of the second module body 330 to face the first-third insertion end connection body 343 and the first-fourth insertion end connection body 344, respectively.

In this case, the first-first insertion end connection body 341 and the first-second insertion end connection body 342 may each be provided with 'upper surface guide protruding members I' extending upward and inserted into the upper surface straight line guide slits G. And the first-third insertion end connection body 343 and the first-fourth insertion end connection body 344 may each be provided with 'lower surface guide protruding members I' extending downward and inserted into the lower surface straight line guide slits G. In this case, respective guide protruding members I can guide the reciprocating rectilinear motion of the first insertion end connection bodies 341, 342, 343, and 344 by moving along the corresponding linear guide slits G.

At one end of each of the first-first, first-second, first-third, and first-fourth insertion end connection bodies 341, 342, 343, and 344, the first-first engaging member 331, the first-second engaging member 332, the first-third engaging member 333, or the first-fourth engaging member 334 may be provided. And, to the other end of each of the first-first, first-second, first-third, and first-fourth insertion end connection bodies 341, 342, 343, and 344, the first operation wire 201, the second operation wire 202, the third operation wire 203, or the fourth operation wire 204 may be connected.

The insertion unit 200 may be provided with an auxiliary connection unit into which a medical procedure instrument used during an endoscopic procedure is inserted.

As one embodiment, the auxiliary connection unit may be formed with a pair of auxiliary insertion parts 510 and 520. At this time, the auxiliary insertion parts 510 and 520 have hollows formed therein to communicate with the inside of the insertion unit 200. In this case, a medical procedure equipment or a suction device may be inserted from the outside through the auxiliary insertion parts 510 and 520, and it can enter the inside of the patient's body through the opening of the insertion end after moving through the inside of the insertion unit 200 in a state where the insertion end is inserted into the body.

Figure 8:
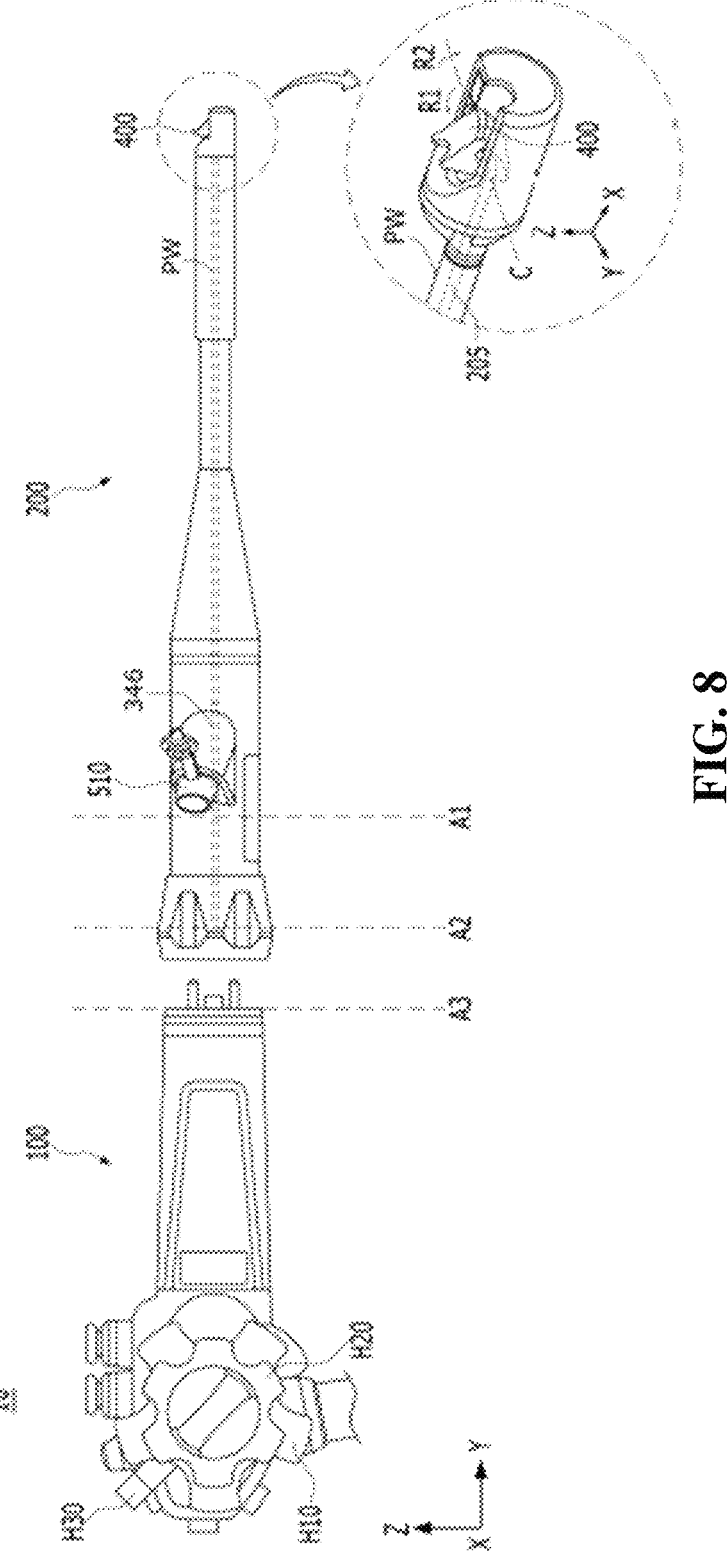
FIG. 8 is a plan view showing an insertion unit according to an embodiment of the present disclosure, and a perspective view showing an enlarged insertion end of the insertion unit.
Figure 9:
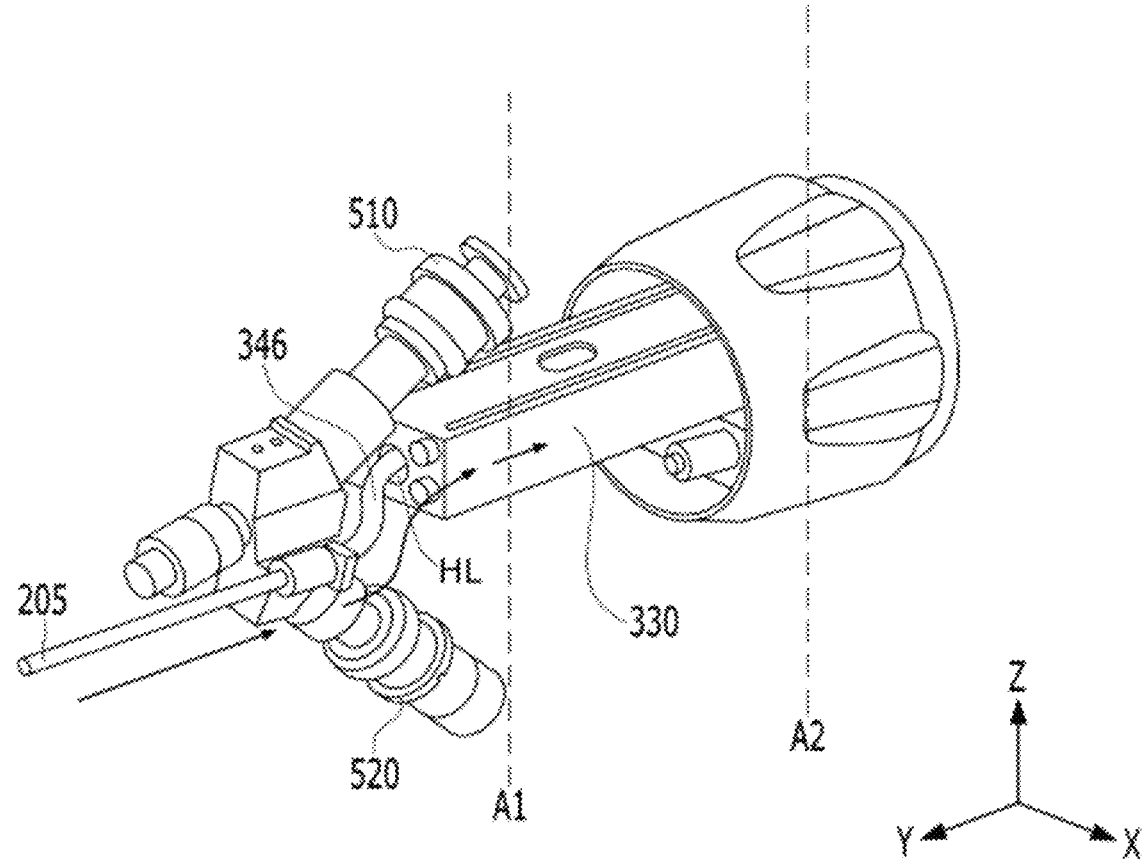
FIG. 9 is a perspective view showing a part of the inside of an insertion unit provided in a detachable endoscope according to an embodiment of the present disclosure.

FIG. 8 is a plan view showing an insertion unit according to an embodiment of the present disclosure, and a perspective view showing an enlarged insertion end of the insertion unit. FIG. 9 is a perspective view showing a part of the inside of an insertion unit provided in a detachable endoscope according to an embodiment of the present disclosure.

Referring to FIGS. 8 and 9, as described above, the force applying module 400 may be disposed at an insertion end of the insertion unit 200. Specifically, the insertion end may have an opening communicating with the outside, and the force applying module 400 may be inserted into the opening. In this case, the force applying module 400 may be formed partially protruding to the outside through the opening.

The fifth operation wire 205 may pass through a curved connection part 346 and extend through an insertion end passage part PW. In this case, the insertion end passage part PW may be coupled to communicate with one end of the curved connection part 346 inside the insertion unit 200, and extend toward the insertion end. The fifth operation wire 205 extending through the insertion end passage part PW may be connected to the force applying module 400, and may transfer the hydraulic pressure supplied from the hydraulic pressure supply part to the force applying module 400.

At this time, the opening of the insertion end may communicate with the second insertion end hollow HL through the insertion end passage part PW and the curved connection part 346 connected thereto. Accordingly, during an endoscopic procedure, contaminants such as blood of a patient may flow into the insertion unit 200 through the opening of the insertion end. Additionally, the introduced contaminants may enter the inside of the operation unit 100 connected to the insertion unit 200. In order to prevent this, the detachable endoscope 10 according to the present disclosure has a structure for preventing the inflow of contaminants, and a detailed description thereof will be provided blow.

Figure 10:
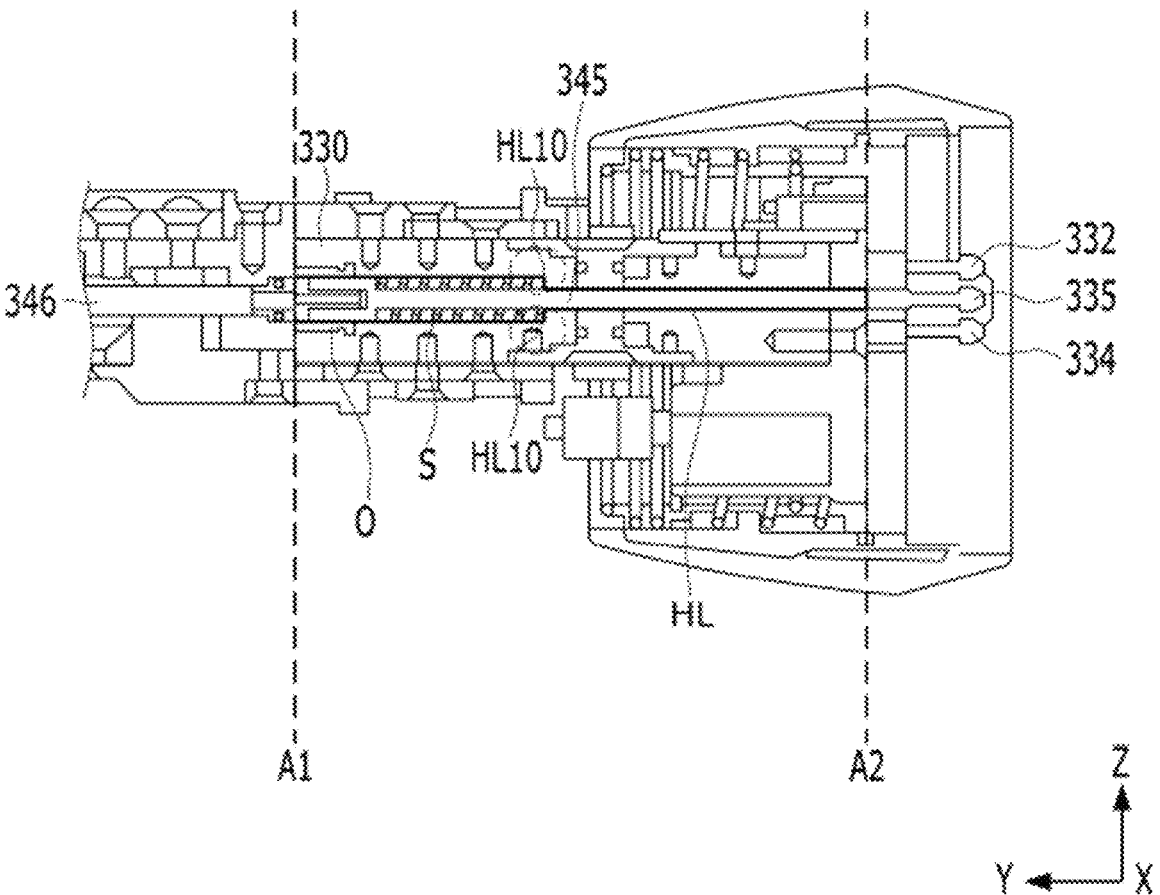
FIG. 10 is a cross-sectional view of a portion of an insertion unit of a detachable endoscope according to an embodiment of the present disclosure.
Figure 11:
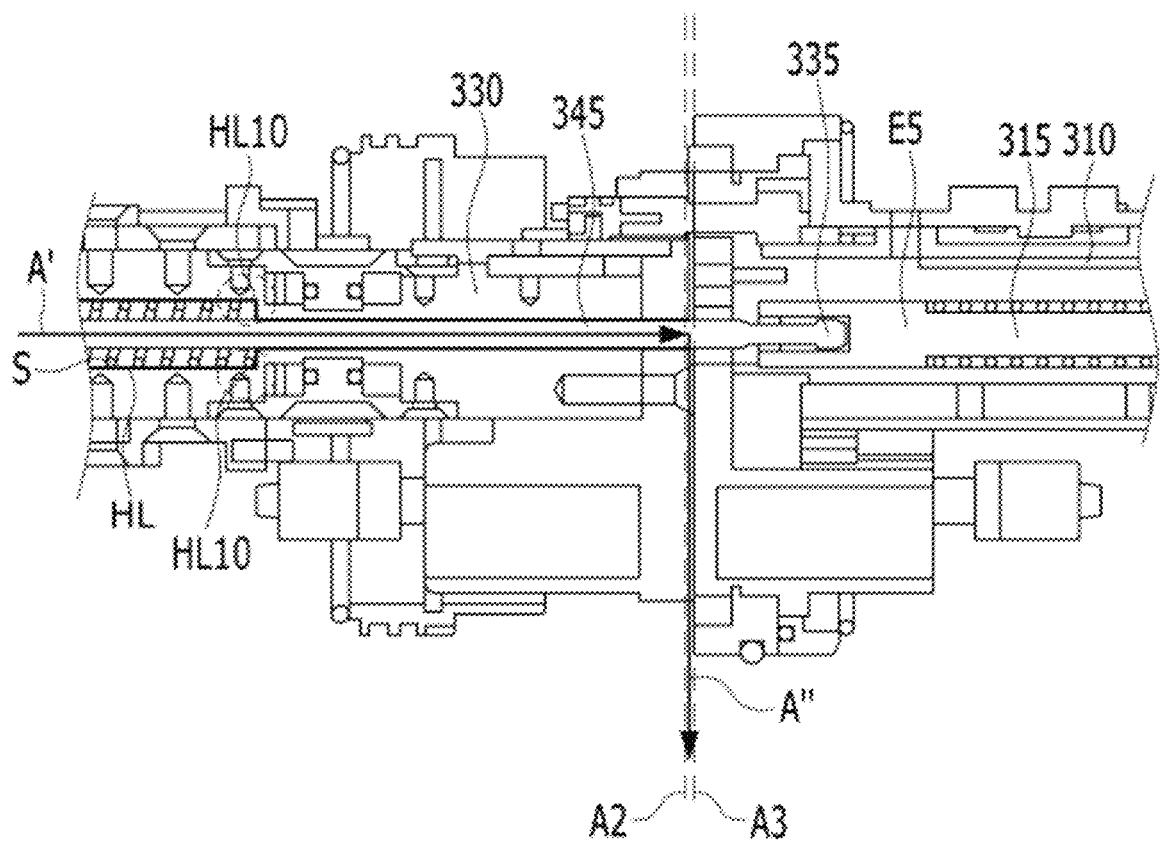
FIG. 11 is a cross-sectional view showing a portion of the detachable endoscope in a state in which the insertion unit and the operation unit are coupled according to an embodiment of the present disclosure.

FIG. 10 is a cross-sectional view of a portion of an insertion unit of a detachable endoscope according to an embodiment of the present disclosure. And FIG. 11 is a cross-sectional view showing a portion of the detachable endoscope in a state in which the insertion unit and the operation unit are coupled according to an embodiment of the present disclosure.

Referring to FIG. 10, the insertion unit 200 may have a hollow formed penetrating both ends of its housing. The hollow may be the first inserted end hollow and/or the second inserted end hollow HL. In this regard, the first insertion end hollow may be provided in two pairs which are spaced apart along the inner circumference direction of the second module body 330 or the housing of the insertion unit 200, and the second insertion end hollow HL may be surrounded by the two pairs of the first insertion end hollows and extend in the longitudinal direction (Y axis direction) passing through the center of them. Additionally, the second insertion end hollow HL is spaced apart from the first insertion end hollows in the housing, so that it can be completely isolated from the two pairs of the first insertion end hollows and cannot communicate with them.

The second insertion end hollow HL may include a stepped part HL10. The stepped part HL10 may be formed to be stepped toward the outer side in the radial direction with respect to the longitudinal direction (Y axis direction) of the second insertion end hollow HL. Due to this stepped part HL10, the second insertion end hollow HL may include a large-diameter part having a relatively larger diameter. In this case, the large-diameter part may be disposed at an end (hereinafter, a first end) among both ends of the second insertion end hollow HL, which is adjacent to the curved connection part 346.

In this case, as described above, the second intermediate connection part 320' may be inserted penetrating the second insertion end hollow HL. In this regard, the second intermediate connection part 320' may be formed to have a diameter substantially equal to the inner diameter of the second insertion end hollow HL. Additionally, among both ends of the second intermediate connection part 320', an end adjacent to the curved connection part 346 (hereinafter, referred to as a first end) may be formed to have a diameter substantially equal to an inner diameter of the large-diameter part of the second insertion end hollow HL. Accordingly, the first end of the second intermediate connection part 320' may be formed to have a larger diameter than other portions of the second intermediate connection part 320'.

In this case, the elastic member S may be disposed between the first end of the second intermediate connection part 320' and the above-described stepped part. As described above, the elastic member S is formed in a spring shape, and the second intermediate connection part 320' is inserted penetrating the elastic member, and at this time, both ends of the elastic member S may be disposed to be caught in contact with the first end of the second intermediate connection part 320' and the stepped part HL10, respectively. Accordingly, when the second intermediate connection part 320' is pulled backward (−Y axis direction) by the third operation part H30, the elastic member S is compressed, and when the force applied to the second intermediate connection part 320' is removed, the elastic member S can provide an elastic restoring force to move the second intermediate connection part 320' back to the front (Y axis direction).

The second insertion end hollow HL may be formed penetrating both ends of the housing of the insertion unit 200 to form a sealed space, while being completely separated from the first insertion end hollows surrounding the second insertion end hollow HL and other components. Accordingly, contaminants introduced through the curved connection part 346 may move only through the inside of the second insertion end hollow HL.

Additionally, sealing members O may be provided at both ends of the second intermediate connection part 320'. The sealing member O seals the fine space between both ends of the second intermediate connection part 320' and the second insertion end hollow HL, so that contaminants flowing through the curved connection part 346 can be prevented from being discharged to the outside. The sealing member O may be, for example, an O-ring made of synthetic rubber or synthetic resin.

As such, the second insertion end hollow HL is formed to seal the space between the portion A1 connected to the curved connection part 346 and the rear end A2 of the second module body 330, so that contaminants introduced through the opening of the insertion end can be guided to flow only through the second insertion end hollow HL while being prevented from flowing out.

Referring to FIG. 11, when the insertion unit 200 is coupled to the operation unit 100, a discharge passage part through which contaminants are discharged may be formed between the first coupling end of the operation unit 100 and the second coupling end of the insertion unit 200.

Specifically, when the insertion unit 200 is coupled to the operation unit 100, a discharge passage part configured as a predetermined clearance part may exist between the first coupling end and the second coupling end. The discharge passage part may be disposed between the rear end A2 of the second coupling end and the front end A3 of the first coupling end.

In this case, as the second intermediate connection part 320' performs reciprocating rectilinear motion along the longitudinal direction (Y axis direction) within the second insertion end hollow HL by the manipulation of the third operation part H30, contaminants flowing in the first movement direction A' can move through the inside of the second insertion end hollow HL, and these contaminants can be discharged to the outside through the rear end opening of the second insertion end hollow HL. In addition, the contaminants discharged to the outside of the second insertion end hollow HL can flow or fall downward along the second movement direction A" by the action of gravity, and can be discharged to the outside of the detachable endoscope 10 through the discharge passage part.

As such, since contaminants are discharged to the outside through the discharge passage part, contaminants introduced into the endoscope 10 during endoscopic procedures can be prevented from being introduced into the operation unit 100. Accordingly, even though the insertion unit 200 is contaminated when an endoscopic procedure is performed, the inside of the operation unit 100 can be prevented from being contaminated. As a result, when the next endoscopic procedure is performed after the previous endoscopic procedure is completed, the procedure can be performed only by replacing the insertion unit 200 with a new unit, while preventing the occurrence of infectious diseases among patients. In addition, it is possible to reuse the operation unit 100, which has a relatively complex structure, such as including the operation module H, and is expensive to manufacture, so the need for washing is reduced, and there may be a great advantage in terms of economy.

As described above, according to the embodiments of the present disclosure, the insertion unit 200 and the detachable endoscope 10 including the insertion unit 200 have a sealed hollow formed inside the insertion unit 200, so that they can induce contaminants such as blood flowing thereinto during an endoscopic procedure to flow only into the aforementioned hollow. Additionally, the contaminants passing through the hollow of the insertion unit 200 are discharged through the discharge passage part formed between the insertion unit 200 and the operation unit 100 when the two units are coupled, so that the inside of the operation unit 100 can be prevented from being contaminated, thereby addressing the cleaning problem of the operation unit 100, and enabling its reuse.

The afore-mentioned description of the disclosure is just an example, and a person having ordinary skill in the art may understand that it can be easily modified into other specific configuration without changing the technical spirit or essential features of the disclosure. Accordingly, it should be understood that the embodiments described above are illustrative in every respect and not restrictive. For example, the respective components described as a singular form may be implemented in a distributed form, and likewise the respective components described as a distributed form may be implemented in a combined form.

The scope of the present disclosure is represented by the following claims, and all modifications and changes derived from the meaning and scope of the claims and equivalent concepts thereof should be interpreted as being included in the scope of the present disclosure.

REFERENCE SIGN LIST

10: Detachable endoscope
100: Operation unit
200: Insertion unit
300: Detachment unit
400: Force applying module

What is claimed is:

1. An insertion unit for a detachable endoscope, the insertion unit comprising:

a housing having a hollow penetrating the housing in a longitudinal direction from a proximal end of the housing to a distal end of the housing, wherein the hollow includes at least one first insertion end hollow and a second insertion end hollow, the second insertion end hollow being spaced apart from the at least one first insertion end hollow within the housing, the second insertion end hollow being isolated from the at least one first insertion end hollow, wherein the second insertion end hollow includes a stepped part having a stepped shape in a radial direction relative to a longitudinal direction of the second insertion end hollow, the second insertion end hollow having a maximum inner diameter at the stepped part;

an insertion end connection part disposed in the second insertion end hollow;

a spring disposed between the stepped part and a distal end of the insertion end connection part, the spring being configured to provide an elastic force to the insertion end connection part; and wherein the insertion end connection part includes a first end portion disposed at the distal end of the insertion end connection part, the first end portion having a diameter substantially equal to the maximum inner diameter of the second insertion end hollow, wherein the insertion end connection part penetrates the spring, and two opposite ends of the spring are in contact with the first end portion of the insertion end connection part and the stepped part, respectively, wherein the insertion unit is configured to have contaminants entering the insertion unit flow only through the second insertion end hollow and discharge to an outside through a rear end opening of the second insertion end hollow.

2. The insertion unit for a detachable endoscope of claim 1, further comprising a curved connection part connected to the distal end of the insertion end connection part and at least one portion of the curved connection part being curved with respect to a longitudinal direction of the insertion end connection part.

3. The insertion unit for a detachable endoscope of claim 1, wherein at the distal end of the insertion end connection part, a sealing ring configured to seal a space between the insertion end connection part and the second insertion end hollow is disposed.

4. A detachable endoscope comprising:

the insertion unit according to claim 1 having one end configured to be inserted into a body;

a controller coupled to another end of the insertion unit and configured to operate the one end of the insertion unit to perform a bending motion; and a detachment unit configured to detachably couple the controller and the insertion unit, the detachment unit having an intermediate connection bar configured to be connected with the insertion end connection part.

5. The detachable endoscope of claim 4, wherein when the insertion unit and the controller are coupled, a discharge passage part is defined between a first coupling end of the controller and a second coupling end of the insertion unit, which are disposed to face each other.

6. A detachable endoscope comprising:

an insertion unit according to claim 2 having one end configured to be inserted into a body;

a controller coupled to another end of the insertion unit and configured to operate the one end of the insertion unit to perform a bending motion; and a detachment unit configured to detachably couple the controller and the insertion unit, the detachment unit having an intermediate connection bar configured to be connected with the insertion end connection part.

7. A detachable endoscope comprising:

an insertion unit according to claim 3, having one end configured to be inserted into a body;

a controller coupled to another end of the insertion unit and configured to operate the one end of the insertion unit to perform a bending motion; and a detachment unit configured to detachably couple the controller and the insertion unit, the detachment unit having an intermediate connection bar configured to be connected with the insertion end connection part.

* * * * *